(12) United States Patent
Sherwood (10) Patent No.: US 9,381,266 B2
(45) Date of Patent: *Jul. 5, 2016

(54) SCENT DEVICES AND METHODS

(71) Applicant: EnviroScent, Inc., Atlanta, GA (US)

(72) Inventor: Jeffrey S. Sherwood, Jasper, GA (US)

(73) Assignee: EnviroScent, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/582,531

(22) Filed: Dec. 24, 2014

(65) Prior Publication Data

US 2015/0108242 A1 Apr. 23, 2015
US 2016/0136317 A9 May 19, 2016

Related U.S. Application Data

(63) Continuation of application No. 11/571,240, filed as application No. PCT/US2005/022566 on Jun. 24, 2005, now Pat. No. 8,919,662.

(60) Provisional application No. 60/582,670, filed on Jun. 24, 2004.

(51) Int. Cl.
*A61L 9/12* (2006.01)
*A01M 1/20* (2006.01)
(Continued)

(52) U.S. Cl.
CPC ............... *A61L 9/12* (2013.01); *A01M 1/2055* (2013.01); *A01N 25/34* (2013.01); *A61L 9/04* (2013.01); *A61L 9/042* (2013.01); *A44C 7/00* (2013.01); *A44C 15/002* (2013.01)

(58) Field of Classification Search
CPC ............ A61L 9/12; A61L 9/127; A61L 9/04; A61L 9/042; A01M 1/20; A01M 1/2022; A01M 1/2027; A01M 1/2055; A01N 25/34; A44C 7/00; A44C 15/002
USPC .................... 239/53–56, 41, 44, 48, 52, 6, 36
See application file for complete search history.

(56) References Cited

U.S. PATENT DOCUMENTS 324,853 A   8/1885   Laurier
855,984 A   6/1907   Russell
(Continued)

FOREIGN PATENT DOCUMENTS

CN   102917878 A   2/2013
EP   1190725 A2   3/2002
(Continued)

OTHER PUBLICATIONS

International Search Report & Written Opinion for corresponding PCT App. No. PCT/US2005/022566, dated Jun. 18, 2007.
(Continued)

*Primary Examiner* — Christopher Kim
(74) *Attorney, Agent, or Firm* — Kilpatrick Townsend & Stockton LLP (57) ABSTRACT

Scent devices and methods are provided. In one embodiment, the present invention can be a device to scent an environment comprising a scent and a structural component. The scent stick can have a length to average cross-sectional diameter ratio of at least about 4:1 according to some embodiments. The scent stick can be colored to blend into an environmental setting to make the presence of the scent stick unobtrusive. The scent stick may also be attached or hung by the addition of a hanger or hoop. The scent stick may be hung from a tree, automobile mirror or a person as an adornment. Other embodiments are also described.

20 Claims, 4 Drawing Sheets

(51) Int. Cl.
*A01N 25/34* (2006.01)
*A61L 9/04* (2006.01)
*A44C 7/00* (2006.01)
*A44C 15/00* (2006.01)

(56) References Cited

U.S. PATENT DOCUMENTS

| | | | |
|---|---|---|---|
| 934,502 A | 9/1909 | Canon |
| 1,777,820 A | 10/1930 | Anenberg |
| 1,878,401 A | 9/1932 | John |
| 1,988,141 A | 1/1935 | Schaller |
| 2,120,204 A | 6/1938 | Langhorst |
| 2,303,073 A | 11/1942 | Brown |
| 2,615,754 A | 10/1952 | Lindenberg |
| 2,626,833 A | 1/1953 | Valentine |
| 2,800,457 A | 7/1957 | Green et al. |
| 3,041,288 A | 6/1962 | Anthony |
| 3,415,758 A | 12/1968 | Powell et al. |
| 3,516,941 A | 6/1970 | Matson |
| 3,575,345 A | 4/1971 | Buck |
| 3,634,564 A | 1/1972 | Ikamoto et al. |
| 3,770,856 A | 11/1973 | Ueki et al. |
| 3,870,542 A | 3/1975 | Ida et al. |
| 3,954,928 A | 5/1976 | Omori et al. |
| 4,020,156 A | 4/1977 | Murray et al. |
| 4,081,384 A | 3/1978 | Pracht |
| 4,210,487 A | 7/1980 | Driscoll |
| 4,234,627 A | 11/1980 | Schilling |
| 4,384,589 A | 5/1983 | Morris |
| 4,753,389 A | 6/1988 | Davis et al. |
| 4,802,626 A | 2/1989 | Forbes et al. |
| 5,103,654 A | 4/1992 | Gee et al. |
| 5,112,688 A | 5/1992 | Michael |
| 5,145,842 A | 9/1992 | Driedger et al. |
| 5,372,303 A | 12/1994 | Paul |
| 5,395,047 A | 3/1995 | Pendergrass |
| 5,437,410 A | 8/1995 | Babasade |
| 5,503,332 A | 4/1996 | Glenn |
| 5,544,812 A | 8/1996 | Torres |
| 5,578,563 A | 11/1996 | Trinh et al. |
| 5,763,038 A | 6/1998 | Wood et al. |
| 5,771,503 A | 6/1998 | Valimaa et al. |
| 6,014,788 A | 1/2000 | Jaffri |
| 6,168,088 B1 | 1/2001 | Mobley |
| 6,183,596 B1 | 2/2001 | Massuda et al. |
| 6,194,375 B1 | 2/2001 | Ness et al. |
| 6,214,163 B1 | 4/2001 | Matsuda et al. |
| 6,248,703 B1 | 6/2001 | Finucane et al. |
| 6,261,483 B1 | 7/2001 | Frank et al. |
| 6,329,057 B1 | 12/2001 | Dungworth et al. |
| 6,575,383 B2 | 6/2003 | Dobler et al. |
| 6,688,551 B1 | 2/2004 | He et al. |
| 6,803,033 B2 | 10/2004 | McGee et al. |
| 6,921,024 B2 | 7/2005 | Donnelly et al. |
| 7,235,261 B2 | 6/2007 | Smith et al. |
| 7,741,266 B2 | 6/2010 | Bell et al. |
| 8,919,662 B2 * | 12/2014 | Sherwood | A01M 1/2055 239/36 |
| 9,132,204 B2 | 9/2015 | McKay et al. |
| 9,149,552 B1 | 10/2015 | Do et al. |
| 2002/0136886 A1 | 9/2002 | He et al. |
| 2003/0024997 A1 | 2/2003 | Welch et al. |
| 2003/0211799 A1 | 11/2003 | Yao et al. |
| 2004/0001891 A1 | 1/2004 | Smith et al. |
| 2007/0187524 A1 | 8/2007 | Sherwood |
| 2007/0224232 A1 | 9/2007 | Sherwood |
| 2008/0008860 A1 | 1/2008 | Murray et al. |
| 2008/0009616 A1 | 1/2008 | Frank et al. |
| 2008/0286143 A1 | 11/2008 | Grodsky |
| 2011/0256364 A1 | 10/2011 | Boyer et al. |
| 2011/0262377 A1 | 10/2011 | McKay et al. |
| 2015/0136872 A1 | 5/2015 | Sherwood |
| 2015/0374869 A1 | 12/2015 | McKay et al. |

FOREIGN PATENT DOCUMENTS

| | | |
|---|---|---|
| GB | 0914421 | 1/1963 |
| GB | 1221488 | 2/1971 |
| GB | 1226448 | 3/1971 |
| GB | 1387265 | 3/1975 |
| JP | 08-289925 | 11/1996 |
| JP | 2000-312712 | 11/2000 |
| JP | 2006-333904 | 12/2006 |
| WO | 9112029 A1 | 8/1991 |
| WO | 98/07405 | 2/1998 |
| WO | 98/47477 | 10/1998 |
| WO | 98/47478 | 10/1998 |
| WO | 9842818 A1 | 10/1998 |
| WO | 99/43667 | 9/1999 |
| WO | 2004020566 A1 | 3/2004 |
| WO | 2006002395 | 1/2006 |
| WO | 2011/123723 | 10/2011 |
| WO | 2013064501 A1 | 5/2013 |

OTHER PUBLICATIONS

Chinese Office Action, with English translation, application No. 2011-80026620.7, mailed Feb. 12, 2014, 12 pages.
International Preliminary Report on Patentability and Written Opinion for corresponding PCT/US2011/30842, mailed May 23, 2011.
Japanese Office Action, with English translation, issued in JP2013-502872, dated Oct. 28, 2014.
Chinese Office Action, with English translation, issued in CN 2011-80026620.7, issued on Nov. 14, 2014.
U.S. Appl. No. 61/319,431, filed Mar. 31, 2010, Sherwood.
U.S. Appl. No. 61/409,627, filed Nov. 3, 2010, Sherwood.
U.S. Appl. No. 61/419,959, filed Dec. 6, 2010, Sherwood.
U.S. Appl. No. 14/866,297, filed Sep. 25, 2015, Do et al.
U.S. Appl. No. 62/173,264, filed Jun. 9, 2015, Mehnert et al.
U.S. Appl. No. 29/534,919, filed Jul. 31, 2015, McKay et al.
U.S. Appl. No. 14/851,763, filed Sep. 11, 2015, McKay et al.
U.S. Appl. No. 60/582,670, filed Jun. 24, 2004, Sherwood.
Chinese Office Action, with English Translation, issued in Patent Application No. 2011-80026620.7, dated Nov. 14, 2014, 15 pages.
Japanese Office Action, with English translation, issued in Patent Application No. JP2013-502872, dated Jun. 30, 2015, 2 pages.
U.S. Appl. No. 11/571,240, Non-Final Office Action, mailed Aug. 5, 2009, 9 pages.
U.S. Appl. No. 11/571,240, Final Office Action, mailed Mar. 23, 2010, 12 pages.
U.S. Appl. No. 11/571,240, Final Office Action, mailed Nov. 2, 2011, 11 pages.
U.S. Appl. No. 11/571,240, Non-Final Office Action, mailed Aug. 2, 2012, 10 pages.
U.S. Appl. No. 11/571,240, Final Office Action, mailed Feb. 4, 2013, 10 pages.
U.S. Appl. No. 11/571,240, Non-Final Office Action, mailed Nov. 25, 2013, 8 pages.
U.S. Appl. No. 11/571,240, Final Office Action, mailed Feb. 13, 2014, 6 pages.
International Patent Application No. PCT/US2005/022566, International Preliminary Report on Patentability, mailed Jul. 10, 2007, 5 pages.

* cited by examiner

SCENT DEVICES AND METHODS

CROSS-REFERENCE TO RELATED APPLICATION

This application is a continuation of U.S. application Ser. No. 11/571,240, filed Dec. 22, 2006, which is a U.S. National Phase application under 35 U.S.C. §371 of International Patent Application No. PCT/US2005/022566, filed Jun. 24, 2005, which claims the priority and benefit of U.S. Provisional Patent Application Ser. No. 60/582,670, filed Jun. 24, 2004, the contents of all of which are incorporated by reference in their entirety.

TECHNICAL FIELD

The various embodiments of the present invention relate generally to scent emitting devices.

BACKGROUND

The volatilization of scent from a substrate has been described previously. Many materials have been described that release a volatile material, such as a scent, including ceramics, polymers, wood and cellulose materials. Cotton has been used to release volatile materials as described in U.S. Pat. Nos. 2,615,754 and 5,372,303. Fabric has also been described as an absorbent medium from which a volatile material can evaporate as described in U.S. Pat. No. 2,626,833. In U.S. Pat. No. 855,984 a sponge is used to volatilize a perfume or disinfectant. U.S. Pat. No. 1,988,141 describes the use of a felt pad to release a perfume. These materials all produce articles that have a very rapid release of the scent from their matrix if unimproved with further restrictions which add significant cost to the articles.

Wood has been used to hold scent in articles like incense. To release significant quantities of the scent, however, the wooden incense sticks are typically burned. Allowing the incense sticks to release their scent without burning results in an inadequate scent release. Additionally, wood is not highly absorbent and therefore absorbs low amounts of scented material. Wood pulp has been used to absorb fragrance and release it, as described in U.S. Pat. No. 2,120,204. The use of wood pulp poses very restrictive uses because it is quite friable and cannot be made into stable rods that resist breaking. Molded plastics have also been used to disperse scents as described in U.S. Pat. No. 4,802,626. The amount of scent that releases from this type of medium in a reasonable time frame is very limited.

Many air fresheners and volatile material dispersers use paper products as a medium from which a scent may evaporate. Commercial examples of these types of air fresheners use a stiff blotter type paper and are produced by Medo Industries, Baltimore, Md. and Little Trees, Watertown, N.Y. U.S. Pat. No. 6,575,383 describes using 120# commercial blotting paper, beverage board type papers, and commercial Cover Stock to absorb a fragrance for freshening air in a bathroom. U.S. Pat. No. 3,575,345 uses a porous paper such as filter paper. Other paper and blotter-based dispersing devices are found in U.S. Pat. Nos. 5,503,332; 5,395,047; 6,168,088; 6,575,383; and 6,688,551.

The major disadvantage of such paper products is that they have a large surface area to volume ratio, a relatively low density or specific gravity, and they release their volatile material too rapidly for many applications. There are descriptions of devices that modify these materials to slow the release rate of the volatile material off of the medium. These modifications have included coating the paper with an occlusive material like a film-forming chemical or a layer of plastic that has limited porosity or alternatively, placing the paper inside an outer covering thereby restricting the vaporization of the scent. While these modifications have shown some effectiveness in slowing the evaporation rate, the modifications add significant cost to the products and require special manufacturing steps.

There are also existing air fresheners that contain a wick structure absorbing a liquid through the wick. Examples of this type of a system are described in U.S. Patent Application 20020136886 and U.S. Pat. Nos. 4,384,589 and 5,437,410. The disadvantage of these types of devices is the high cost and necessity for multiple components.

What is needed are devices for providing scents that are durable, easily manufactured and provide a slow release of scent for many applications.

SUMMARY

The present invention comprises methods and devices for providing scent. The devices comprise at least two components, a structural component and a scent. The structural component may be formed into a rod shape or may be formed into any shape desired for a particular application. The scent is incorporated into or on the structural component. The device is referred to herein as a scent stick, which is not to be seen as limiting the structure of the device or limiting the scent composition. The devices may optionally further comprise dyes, coating elements, holder elements or attachment elements.

The scent dispersing devices and methods provide for the slow release of a scent, such as a volatile material, and usually without significant or specialized modifications that add to cost to the device. The present invention comprises devices to scent an environment comprising an absorbent material in a rod-like shape having a ratio of length to average cross-sectional diameter of at least about 4:1. The absorbent rod may be made with a specific gravity of greater than about 0.95, The higher specific gravity of the scent stick allows for the slow release of a scent from the rod. This slow release provides an advantage to typical paper air freshener products. The rod may be treated with a colorant. A useful dye is one that is substantive to the rod and may not transfer to another object upon contact. Lake dyes are suitable materials that provide low transfer potential. The scent stick may be colored before, at the same time, or after the scent is incorporated with the rod.

Embodiments of the present invention may be used in floral arrangements to boost the odor of live flowers. Alternatively, a scent stick according to some embodiments of the present invention may be used in with artificial flowers to impart odor to the arrangement. A scent stick may also be provided with an attachment element to allow the scent stick to be hung or attached. For example, by providing a hanger as the attachment element on the scent stick, the scent stick may be hung on a live or artificial tree to impart odor to the tree. The scent stick may also be hung in an automobile, for example, from the rearview mirror, using a hook or string. The scent stick may also be attached to a car vent using a clip apparatus or used as a personal adornment.

Methods of the present invention comprise providing at least one scent stick in an environment, wherein the scent is slowly released from the scent stick into the environment. The scent is slowly released and provides scent to the environment. The scent stick or a combination of scent sticks may be provided to an environment such as a plant or flower arrangement, as a room or vehicle scenting device, for scenting any enclosed or interior space, and for scenting a desired area in an exterior space. Methods of the present invention also comprise making scent sticks.

DETAILED DESCRIPTION

The present invention comprises methods and devices for providing scent. The devices of the present invention are referred to herein as a scent stick, though the use of the term "stick" is not to be seen as limiting the shape or form of the device. The use of the term "scent" is not to be seen as limiting the scent material to only materials that have a scent, but includes other compounds that are not detectable as a scent by humans. The devices of the present invention comprise at least a structural component and a scent. Optionally, the devices may further comprise dyes, coating elements, holder elements or attachment elements.

Methods of the present invention comprise making and using scent sticks. Methods of use comprise providing one or more scent sticks to an environment. The one or more scent sticks slowly release scent to the environment. The scent sticks release scent to the environment for at least 24 hours, for at least 2 days, for at least 5 days, for at least 10 days, for at least 20 days, for at least 30 days, and in some embodiments, for greater than 30 days, and all ranges in between. Methods of making a scent stick comprise providing a structural component, such as a rod or shaped form made of an appropriately absorbent material; and in no particular order, applying a scent, such as a volatile material, to structural component, and optionally, dying the structural component a particular color or colors, or applying a pattern to the structural component. The scent stick may or may not be colored. The method may further comprise applying or attaching a coating element to a portion or the entire surface of the scent stick. The method may comprise affixing an attachment element to the scent stick. The method may further comprise providing the scent stick in a holder element. The method may further comprise packaging the scent stick, so that the scent is not released in the environment.

Figure 1:
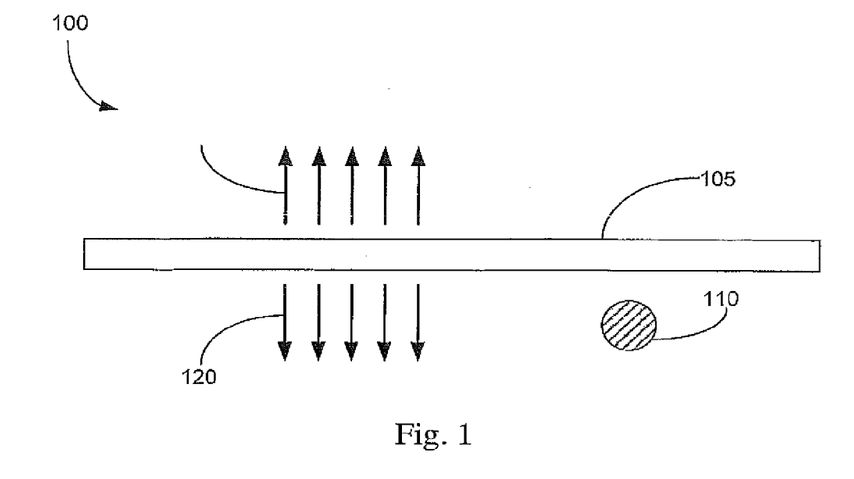
FIG. 1 illustrates an embodiment of the present invention.

Referring now to the figures, FIG. 1 illustrates an embodiment 100 of the present invention. As shown, embodiment 100 comprises a scent stick 105. As used herein, scent stick 105 may be a scent member, scent rod, or any other material in any shape that is capable of emitting a scent composition. For the purpose of the present invention a scent is defined as any material, such as a volatile material, that may provide a benefit including fragrance, perfume, essential oil, solvent, deodorizer, malodor counteractant, insect repellant, and antimicrobial, insecticide, or pesticide activity. The material containing scent may be a solid, liquid, or gel or any form that can be incorporated into or applied to the structural component and release scent from the structural component when exposed to ambient air.

Scent stick 105 may be made with any material capable of absorbing or incorporating therein or thereon a scent and releasing the scent when exposed to ambient environmental conditions. The term absorbent as used herein means the ability of the structural component of the scent stick to absorb at least about 10% of its weight in scent, at least about 20%, at least about 30%, at least about 40%, at least about 50%, or at least about 75% of its weight in scent. In one embodiment, the scent stick will release at least about 30% by weight of the original amount of scent within the first 30 days of exposure to the ambient air. In an embodiment, the scent stick will release at least about 30% by weight of the original amount of scent within the first 30 days of exposure to the ambient air. In an embodiment, the scent stick will release at least about 10% by weight of the original amount of scent within the first 5 days of exposure to the ambient air. In an embodiment, the scent stick will release at least about 30% by weight of the original amount of scent within the first 50 days of exposure to the ambient air.

In an embodiment, scent stick 105 may be a compressed paper rod, while in other embodiments, scent stick 105 may be any other material capable of absorbing a scent through contact and releasing the absorbed scent over time, and includes but is not limited to, plastic, cardboard, or fabric. Scent stick 105 may be of any desired length and/or shape depending upon the application. In some embodiments, scent stick 105 may be a cylindrical rod having a circular-cross section 110 but scent stick 105 may also have any cross-sectional shape. For example, scent stick 105 may be oval or rectangular in shape. Scent stick 105 may also be made at various lengths in the embodiments of the present invention. Scent stick 105 may have any combination of shapes and sizes, and an example is a form such as a candy cane. Scent stick 105 may have a diameter similar to the diameter of a flower stem in some embodiments or may have other diameters or cross-sectional areas in other embodiments. In a preferred embodiment the scent stick can have a length to average cross-sectional diameter ratio of at least about 4:1. For applications such as flower arrangements the length to average cross-sectional ratio can be between about 15:1 to about 60:1.

The structural component of the scent stick is stable, in that the structural component of the scent stick does not readily decompose, fall apart, unravel, shred, fracture, break or tear. Once formed, the structural component is sufficiently sturdy to undergo coloring or scent application and to remain substantially intact while exposed to the environment. Embodiments of the present invention generally have a stable nature. Thus, the embodiments of the present invention scent stick are not brittle or friable to the touch. Handling the scent sticks in a typical use or manner does not cause breakage or pieces to dislodge from the scent stick. This feature is an advantage when compared to wood-pulp type products.

Scent sticks may be characterized by their density or specific gravity. Pure water is the base line for specific gravity, and pure water has a density of 1 cubic meter=1000 kg, with a specific gravity of 1. The specific gravity of all other materials is compared to water as a fraction of heavier or lighter density. The specific gravity of a substance is a comparison of its density to that of water. As specific gravity is just a comparison, it can be applied across any units. Table 1 shows the comparison of densities of typical paper air fresheners. Typical paper air fresheners, including common commercial products, have a density (specific gravity) of from about 0.5 to 0.8 before a scent is added. Common woods have a density (specific gravity) of from less than 0.2 for balsa wood to less than 0.95 for oak. The density (specific gravity) of pine is typically between 0.35-0.66. In an embodiment, the density (specific gravity) of the structural component is greater than about 0.95 before scent is added to the structural component. This relatively high density (specific gravity) of the present invention is an advantage as it allows for the slow release of a fragrance from the article over a period of time.

TABLE 1

Density (specific gravity) of commercial paper air fresheners.

| Air Freshener Manufacturer | Density (specific gravity) |
|---|---|
| Orlandi | 0.80 |
| Car Freshener | 0.51 |
| Yankee Candle | 0.43 |
| Gold Canyon | 0.82 |

As shown in FIG. 1, scent stick 105 may be shaped similar to a flower stem and may emit a predetermined scent in the direction of arrows 110 and 115. Scent stick 105 may be impregnated with any scent, scent combination, or fragrance that a user may desire, or the scent stick may be coated with a scented substance or made with scented materials. These scents may be floral scents or may be any other scents including, but not limited to natural or synthetic scents, scents that mimic scents found in nature, and scents that are not found naturally occurring in plants. Such scents may include rose, iris, strawberry, coffee, peppermint, chocolate, vanilla, lavender, lemon, fresh flowers, pizza, pine, cinnamon, and jasmine. Additionally, the scent composition may contain one or more essential oils with or without a fragrance. The scent composition may contain a pesticide or insect repellant such as DEET or a synthetic pyrethroid. The scented oils and gels used with the various aspects of this invention are desirably made with natural non-hazardous materials. Additionally, it is desireable that the scented oils and gels allow users to safely handle the scent sticks and easily exchange one scent stick for another scent stick.

Scent stick 105 may also be dyed in some embodiments of the invention so that the scent sticks blend in with the surrounding environment. Suitable dyes for use in the present invention include water-resistant dyes, oil-resistant dyes, and combinations of water- and oil-resistant dyes. In one embodiment where the scent stick is used with fresh or freshly cut flowers and the flowers are placed in water, a water-resistant or combination water-and oil-resistant dye can used. In an embodiment where the scent stick is used with silk flowers or any other material that may absorb an oil, a dye is used that is oil-resistant or both water- and oil-resistant can be utilized. When the scent stick may be used either with fresh flowers or silk flowers, an embodiment may comprise a dye that is both water- and oil-resistant.

Suitable water-resistant dyes include oil soluble dyes and wax soluble dyes. Examples of oil soluble dyes that are suitable for use in the present invention include Pylakrome Dark Green and Pylakrome Red (Pylam Products Company, Tempe Ariz.). Suitable oil-resistant dyes include water soluble dyes. Examples of water soluble dyes that are suitable include FD&C Blue No. 1 and Carmine (Sensient, St. Louis, Mo.). Where the scent stick may be used in aqueous environments, such as with either fresh cut or artificial flowers, a suitable dye is a dye that does not interact substantially with either the fresh cut flowers or the artificial flowers. A suitable dye for this application is a Lake type dye. Examples of Lake dyes are Cartasol Blue KRL-NA LIQ and Cartasol Yellow KGL LIQ (Clariant Corporation, Charlotte, N.C.). Pigments may also be used in coloring the structural component. Such coloring or dying methods are known to those skilled in the art, and any suitable dyes, pigments or colorants are contemplated by the present invention.

A water-resistant dye may be typically dissolved in a hydrophobic solvent. Suitable hydrophobic solvents include Isopar M, petroleum distillates, mineral oil, short or long chain alcohols, fragrances, fragrance raw materials, essential oils and other hydrophobic liquids that will solubilize the dye. In one embodiment, the fragrance used to scent the scent stick can be used to solubilize the water-resistant dye. An oil-resistant dye may be solubilized using a hydrophilic solvent. Suitable hydrophilic solvents include water, short chain alcohols, short chain carboxylic acids and glycols. A combination oil- and water-resistant dye can be solubilized in a solvent into which it will dissolve. Suitable materials include short chain alcohols. In a method of making the scent stick, methanol is used to dissolve and solubilize a Lake dye.

In some embodiments, scent stick 105 may be dyed green so that when scent stick 105 is placed in a flower arrangement bouquet scent stick 105 is not easily visible. In some embodiments the scent stick may be brightly colored to stand out against the background. Still yet in other embodiments, the scent stick 105 can be colored with multiple colors such that the scent stick has various designs and colors.

The scent stick may be wrapped or sleeved with a colored material to disguise the stick to look like a stem or other plant or flower part or to impart a look that is desirable. The wrapping or sleeving can be done using a floral tape, ribbon or other flexible matrix. The sleeve should preferably have sufficient porosity or openings to allow dispersion of the scent through the sleeve. Scent can be absorbed onto the wrapping material as an alternative to absorbing the scent directly onto the stick.

Figure 2:
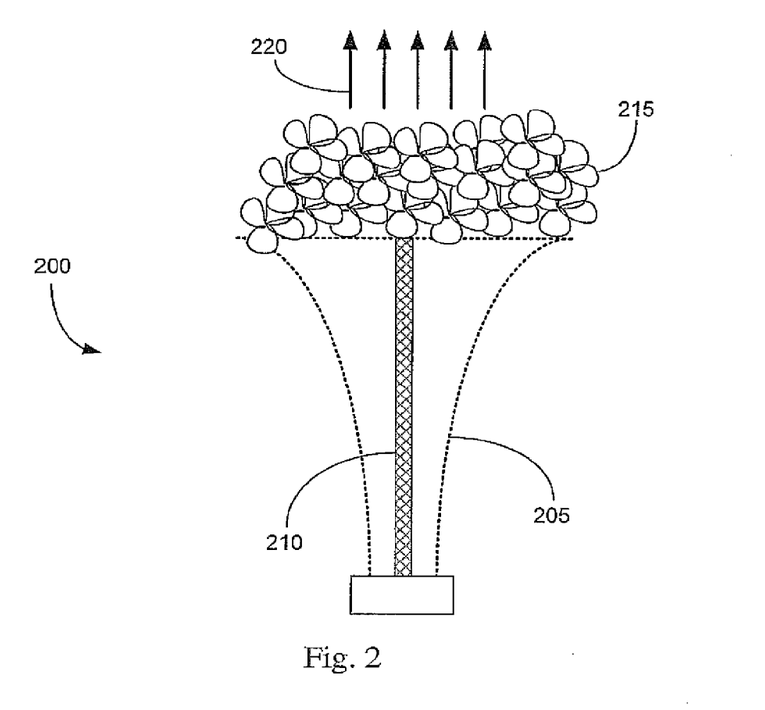
FIG. 2 illustrates an embodiment of the present invention utilized in a floral arrangement.

FIG. 2 illustrates an embodiment 200 of the present invention utilized in a floral arrangement. A floral arrangement may include, but is not limited to, any fresh flower arrangement, live plants, flower cuttings, and artificial flower, plant or plant parts arrangements, including plastic and silk flowers. As shown, embodiment 200 may generally comprise a vase 205, scent stick 210, and a plurality of flowers 215. Although this embodiment is shown in vase 205, scent stick 210 may be used in any other floral arrangement including hand held bouquets, living floral arrangements, and table-top displays. Additionally, some embodiments of the present invention may also be used with other visual arrangements and decorations including silk flowers, table centerpieces, potpourri arrangements, indoor gardens, indoor plants, or any other arrangements or displays that a user may want to enhance with various fragrances.

In embodiment 200, scent stick 210 has been placed inside of vase 205 similar to the general direction of the stems of flowers 215. Scent stick 210 may also be orientated differently in other embodiments so that the entire surface area of scent stick 210 is closer to the top of vase 210 enabling a greater emission of scent from scent stick 210. Scent stick 210 may also be dyed green so that it blends in with the flower stems, but scent stick 210 may also be dyed any other color or combination of colors.

Although, vase 205 is shown with a single scent stick, some embodiments of the present invention may include multiple scent sticks saturated with the same scent or with multiple scents. Arrows 220 generally depict the direction in which scent stick 210 may emit a floral scent to enhance the natural floral scent emitted by flowers 215. Other embodiments of the present invention may also expose the surface area of scent stick 210 so that scent stick 210 may also emit scents in all directions. Additionally, in some embodiments, scent direction may be controlled by putting a scent composition at a passive location, providing openings in a covering layer over the scent stick, or diffusion in the air from all surfaces.

Figure 3:
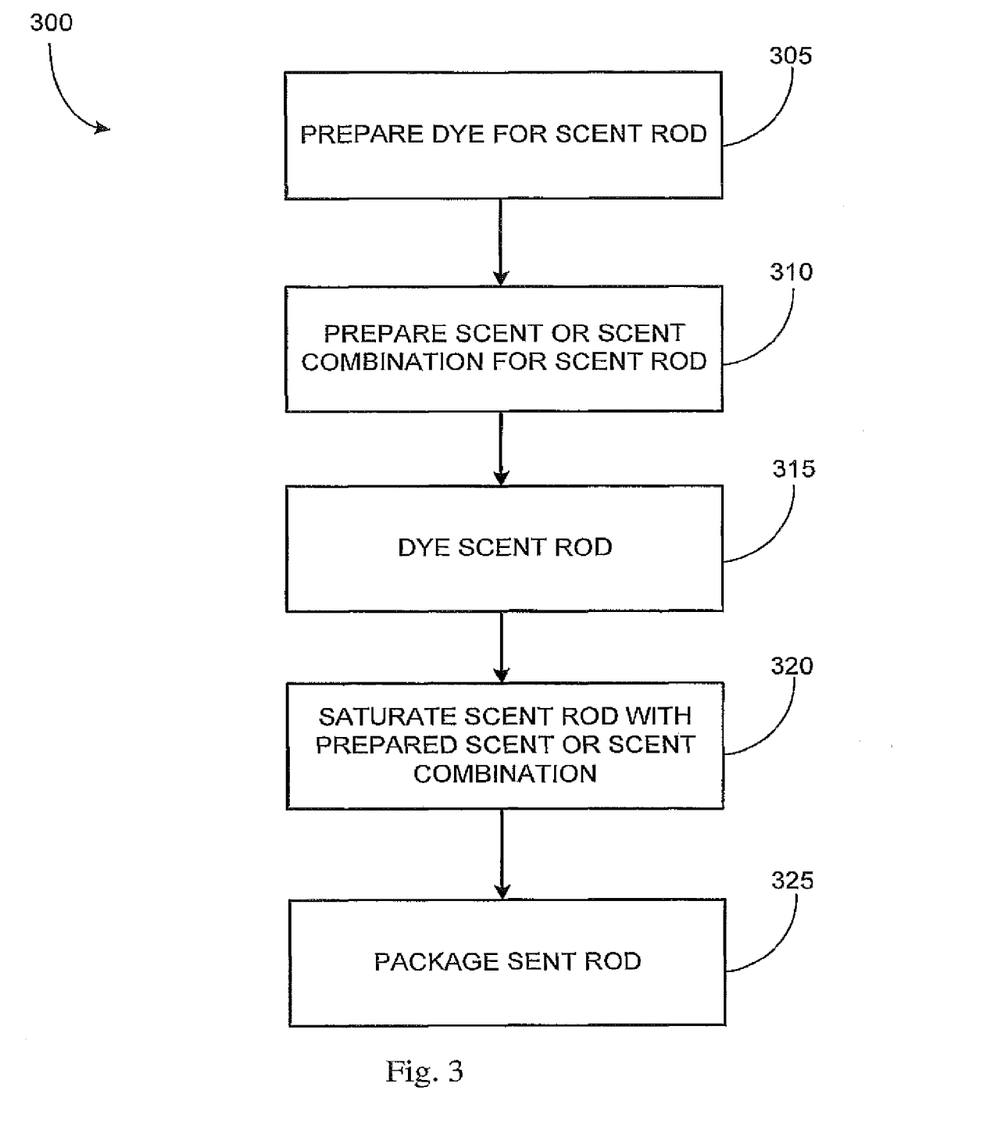
FIG. 3 illustrates a method of making an embodiment of a scent stick.

FIG. 3 illustrates a method of making a scent stick according to an embodiment of the present invention. At 305, a color dye may be prepared to dye a scent stick so that the scent stick may blend into a surrounding environment. For example, a scent stick may be dyed to have the visual appearance of a candy cane so that a scent stick may blend in with other holiday decorations and emit holiday fragrances. At 305 the dye is dissolved in a solute. The nature of the solute to be used is dependant upon the nature of the dye and the application of the scent stick. If the scent stick is to be used with fresh flowers, live plants or fresh cuttings then the dye to be used is typically a water-resistant dye or a water- and oil-resistant dye. If the scent stick is to be used with silk plastic or fabric then the dye used is typically an oil-resistant dye or a water- and oil-resistant dye.

At 310, a fragrance or fragrance combination which is referred to herein as a scent composition or scent may-be prepared so that the structural component of a scent stick may be saturated or impregnated with the scent composition. The scent or scent composition may be made from fragrance oils, scented gels, or any other scents capable of being absorbed by a scent stick. A scent may use alone, or the scent may be combined with other volatile materials such as a pesticide, insect repellant, antimicrobial material or deodorizer or the volatile material may be used alone, to form a scent or scent composition. Both fragrant scents and fragrant scents in combination with other volatile materials, and volatile materials without frangrances are contemplated in the present invention and the selection of which scent is used is generally determined by the intended use.

Next at 315, a scent stick may be dyed for a predetermined amount of time so that the scent stick may blend into its environment. The total dying time may depend upon the material which comprises the structural component of the scent stick and the density of the material. For example, the dying time for a paper-stick scent stick may take less than a minute to a few minutes while a cardboard or plastic paper stick may have longer dying times. Also, the amount of dye used to dye a scent stick may also vary depending upon the material used to construct the scent stick. Some embodiments of the present invention utilizing paper-stick scent sticks may only utilize approximately one (1) gram of dye, but this amount may vary depending upon the length, cross-sectional area, and density of the scent stick. The dye amount may also vary due to the absorption characteristics of structural component materials and dye types. The scent stick may or may not be dried after the dye has been absorbed.

The scent stick may be combined with a prepared scent or scent combination composition at 320 by placing the structural component in intimate contact with the scent composition. The interaction time may depend on the type of scented fragrance applied to the structural component, or how strong or intense of a scent a user wants the scent stick to emit, and/or the type of material used to manufacture the structural component. In some embodiments, a paper structural component may be saturated with a composition comprising approximately one (1) to three (3) grams of one or more scent compositions and the saturation time may range from less than one minute to a few minutes. Other embodiments may utilize more or less amounts of scented compositions to adequately scent a structural component, and may contain various scents with various intensities. Also, other embodiments of the present invention may require longer or shorter saturation times depending upon scent density, structural component material, and other scent stick physical characteristics. When the dye is solubilized in the scent itself as in the case of a water-resistant dye, steps 315 and 320 can be combined.

After adequately saturating a structural component with one or more scent compositions, a scent stick may be packaged at 325. In one embodiment the scent stick is allowed enough contact time between the scent composition and the structural component for the surface of the structural component to be essentially dry to the touch, which minimizes transfer of scent and/or dye when handling. A scent stick may be packaged to preserve the saturated scent or scent combination so that ambient air does not contact the scent stick and allow the scent to escape from the scent stick. Many types of packaging material are capable of protecting the dyed and/or saturated scent stick. One embodiment uses packaging materials through which the scent does not substantially diffuse or evaporate. Suitable materials for packaging the scent stick include cellophane, polypropylene, acrylic, plastics, PET, polymers, fluorinated polyethylene, metalized films, metal, glass, glazed ceramics, and any other impervious material. A useful packaging material includes, but is not limited to, oriented polypropylene, PET, or cellophane. Although method 300, has been described with reference to FIG. 3, it should be noted that other methods of preparing a scent stick exist including that a structural component may be saturated with a scent before being dyed, and that steps of method 300 can be performed in any order that results in a scent stick or steps may be eliminated.

The scent stick may include an attachment element for attaching a scent stick to other objects. In one embodiment, the attachment element is a hook. The scent stick has a hook attached to one end so that it may be hooked or attached permanently or temporarily to an object. In another embodiment, the attachment element is a clip, and the scent stick includes a clip for attaching it to an object. The clip may have an adhesive that can be used for attaching to an object permanently or semi-permanently to an object, or the clip may have a hook and eye region, such as a Velcro strip, that can be used to attach the scent stick to an object. Additionally the clip may have means to temporally attach the stick to a vent or other opening through which air can pass. It is also useful to allow for attachment elements where the scent stick may be removed and replaced with a fresh scent stick when the user so desires, whether or not the attachment element is removed from its attached site.

Figure 4:
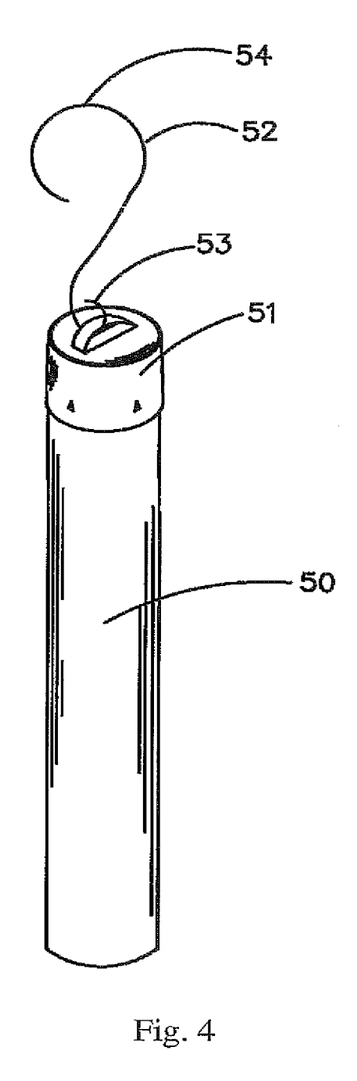
FIG. 4 illustrates a perspective view of one embodiment of the present invention.

The clip can enable the scent stick to be adapted for other applications and uses. For example, the clip can have two or more prongs which can be placed over a louver on a vent allowing for temporary attachment. In one embodiment, the scent stick has a string attached to the scent stick as an attachment element, so that the scent stick can be hung from an object. For example, the string is made of an elastic material. The object to which a scent stick may be attached or hung includes, but is not limited to, people, walls, doors, cabinets, closets, trees, wreaths, auto rearview mirrors, and car and home vents. It is useful if the scent stick is placed in such a manner so that the stick does not touch any surface that might be damaged by being in close proximity to a fragranced material. FIG. 4 illustrates one embodiment of the present invention wherein scent stick 50 can be hung from an object. Attachment element Hook 52 attaches to connector 51 at end 53 and is hung over an object by end 54. In one embodiment the scent stick is attached to a person and worn as an earring or other adornment. In this embodiment the hook may be used to allow the scent stick to be attached to a person's ear or another other part of a person's body. Multiple sticks may be attached to one attachment element, such as hook 52.

Figure 5:
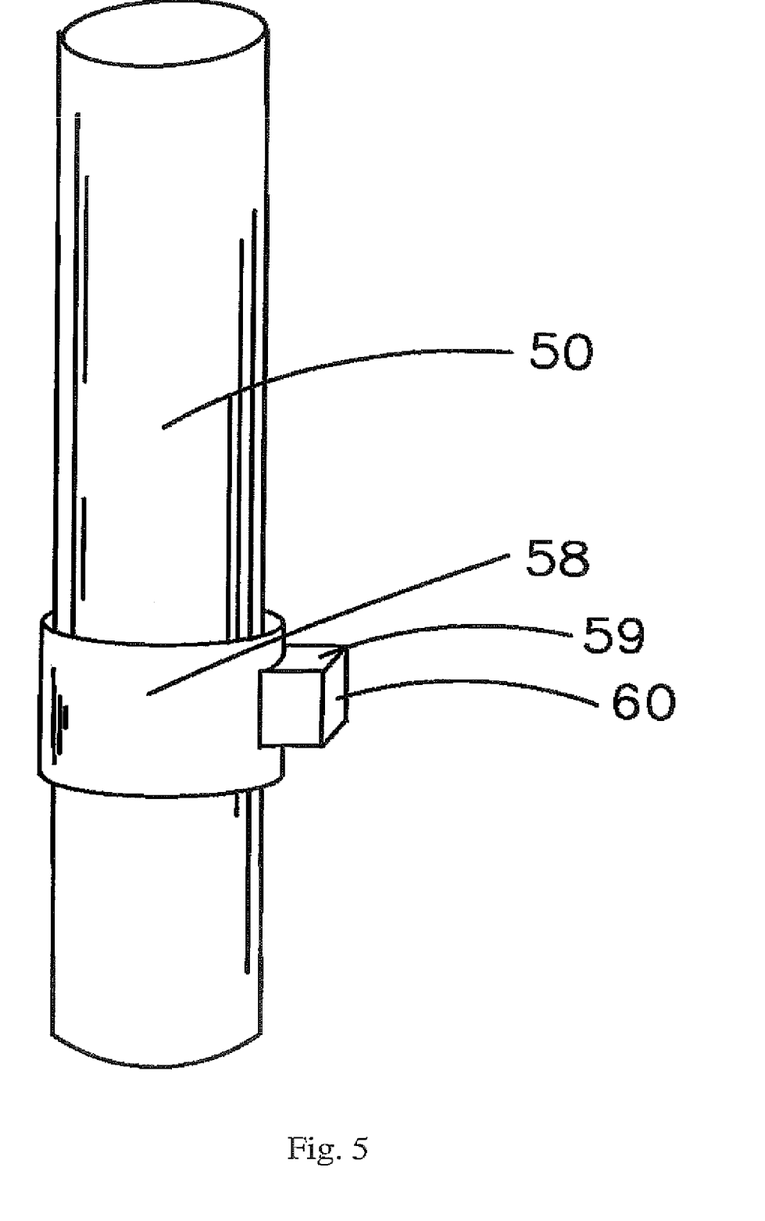
FIG. 5 illustrates an embodiment of a scent stick attached to a clip.

FIG. 5 illustrates one embodiment of the present invention wherein scent stick 50 is attached to clip 58, an attachment element. Clip 58 has side post 59 that has surface 60 onto which an adhesive can be provided enabling the scent stick 50 to be temporally or permanently attached to a surface or object, such as a wall, door, or cabinet. Side post 59 may also mate with another piece which is temporally or permanently attached to a surface or object.

Scent sticks may be placed in individual or multiple holders. The use of such a holder is beneficial to prevent contact between the scent stick and other surfaces. Materials which are useful for a holder should not absorb and transmit a scent onto a surface. Suitable materials for this include metal, ceramic, glass, plastic, and polymers. Some materials that might not be otherwise suitable can be made suitable by coating at least a portion of the holder with a barrier that prevents contact between the holder and the scent stick. The holder may be capable of holding one or more scent sticks. For holders capable of holding one or more scent stick, the same scent or different scents may be placed into the holder at the same time.

One or more scent sticks may be placed into a drawer or other closed or semi-closed space, including interior spaces, and also exterior spaces. In a preferred embodiment the stick or sticks may be placed into a container that has openings to allow the dispersion of the fragrance. One suitable container is a porous or mesh bag.

The present invention comprises methods for making and using scent sticks. A scent stick of the present invention may comprise at least one scent and a structural component comprising an absorbent material shaped into stable rod with a length to average cross-sectional diameter ratio of at least about 4:1. A scent stick may release the scent as various rates, including at least about 30% of the scent evaporates from the rod within about 30 days when in use. The scent evaporates from, or is released by, the structural component of the scent stick. Any mechanism of release of scent, whether by evaporation or other mechanisms, is contemplated by the present invention. Scent sticks of the present invention are capable of releasing a scent into an environment, and may comprise at least one scent and a structural component comprising an absorbent material formed by wrapping a sheet of porous material about a central axis forming a rod or cylindrical article and a scent. A rod-shaped scent stick may comprise a scent, wherein at least about 30% of the scent evaporates from the scent stick within 30 days when the scent stick is exposed to air having a temperature of from about 70-80.degree. Fahrenheit. A scent stick, comprising a structural component and at least one scent, may be formed by the structural component comprising paper wound into a rod shape prior to the introduction of the scent. A scent stick, comprising scent and a structural component that may be formed from multilayers of paper so that the structural component has a density (specific gravity) of greater than about 0.95 before scent is incorporated. Scent sticks of the present invention may be colored with a colorant. It is useful if the colorant does not substantially leach out during handling or use. The colorant may be a lake dye, an oil soluble dye or a water soluble dye. A colorant may printed onto the structural component or the scent stick. The at least one scent may be a fragrance, essential oil, perfume, pesticide, insect repellant, antimicrobial, deodorizer or a mixture or a combination thereof. The structural component may comprise paper or other material derived from a tree or plant. The paper may a low acid paper. The scent stick may comprise an attachment element. The attachment element may be a clip, a hook, a string or other hanging feature, and the string may be elastic. At least one scent stick may be provided within a container or bag that has openings through which the scent may pass. At least one scent stick may be provided in a live or artificial floral arrangement. At least one scent stick may be provided in a drawer containing clothing or fabrics. At least one scent stick may be attached to a person or inanimate object. At least one scent stick may be provided in a holder. A scent stick may be made by providing a structural component, and in no particular order, dying the scent stick and applying a scent composition to the scent stick, and optionally, packaging the scent stick.

It must be noted that, as used in this specification and the appended claims, the singular forms "a", "an", and "the" include plural referents unless the context clearly dictates otherwise. All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention are provided herein, the present invention is not limited to these embodiments. There are numerous modifications or alterations that may suggest themselves to those skilled in the art. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

What is claimed is:

1. A rod assembly comprising:
   a scented rod comprising:
      a sheet of porous paper wound about a central axis to form a multilayered paper rod having a final length to average cross-sectional diameter ratio of at least about 4:1;
      at least one fragrance absorbed by the porous paper; and
   a vase sized and dimensioned to receive the scented rod and to hold the scented rod in a substantially vertically orientation.

2. The rod assembly of claim 1, comprising multiple scented rods, and wherein the vase is sized and dimensioned to receive the multiple scented rods and to hold the multiple scented rods in a substantially vertical orientation.

3. A rod assembly comprising:
   a scented rod comprising:
      a sheet of porous paper wound about a central axis to form a multilayered paper rod having a final length to average cross-sectional diameter ratio of at least about 4:1;
      at least one fragrance absorbed by the porous paper; and
   an artificial tree or a wreath sized and dimensioned to receive the scented rod and to hold the scented rod in a substantially vertically orientation.

4. A rod assembly comprising:
   multiple scented rods, each rod comprising:
      a sheet of porous paper wound about a central axis to form a multilayered paper rod having a final length to average cross-sectional diameter ratio of at least about 4:1;
      at least one fragrance absorbed by the porous paper; and
   a holder that is sized and dimensioned to receive the multiple scented rods and to hold the multiple scented rods in a substantially vertical orientation, the holder formed of a material that does not absorb the at least one fragrance from the multiple scented rods.

5. The rod assembly of claim 4, wherein the holder defines an opening that is sized and dimensioned to receive the multiple scented rods.

6. The rod assembly of claim 5, wherein the opening is sized and dimensioned to hold the multiple scented rods in a substantially vertical orientation.

7. The rod assembly of claim 4, wherein each of the multiple scented rods is configured to be hung from the holder.

8. The rod assembly of claim 4, wherein the holder is configured to prevent contact between the multiple scented rods and a surface on which the holder is placed.

9. The rod assembly of claim 4, wherein the holder is formed of ceramic.

10. The rod assembly of claim 4, wherein a scenting surface of at least one of the multiple scented rods is in direct contact with the holder.

11. The rod assembly of claim 4, wherein the at least one fragrance comprises a perfume.

12. A method comprising:
   disposing multiple scented rods into a holder in a substantially vertical orientation,
   wherein each rod comprises:
      a sheet of porous paper wound about a central axis to form a multilayered paper rod having a final length to average cross-sectional diameter ratio of at least about 4:1;
      at least one fragrance absorbed by the porous paper; and
   wherein the holder is formed of a material that does not absorb the at least one fragrance from the multiple scented rods.

13. The method of claim 12, wherein disposing the multiple scented rods into a holder comprises disposing the multiple scented rods into a vase.

14. The method of claim 12, wherein disposing the multiple scented rods into a holder comprises disposing the multiple scented rods into an artificial tree or a wreath.

15. The method of claim 12, wherein disposing the multiple scented rods into a holder comprising hanging each of the multiple scented rods from the holder.

16. The method of claim 12, further comprising removing the multiple scented rods from packaging prior to disposing the multiple scented rods into the holder.

17. The method of claim 12, wherein the at least one fragrance comprises a perfume.

18. A scented device comprising:
   a sheet of porous paper wound about a central axis to form a multilayered paper rod having a final length to average cross-sectional diameter ratio of at least about 4:1;
   at least one fragrance absorbed by the porous paper; and
   an attachment element, the attachment element including:
      a ring element disposed around a circumference of the multilayered paper rod; and
      a post connected to the ring element and extending radially outward from the ring element.

19. The scented device of claim 18, further comprising an adhesive material disposed on a surface of the post.

20. The scented device of claim 18, wherein the post is sized and dimensioned to mate with a receiving element to attach the multilayered paper rod to the receiving element.

* * * * *